United States Patent [19]
Freitas

[11] Patent Number: 5,549,595
[45] Date of Patent: *Aug. 27, 1996

[54] GEAR ACTIVATED TROCAR ASSEMBLY

[75] Inventor: Michael W. Freitas, Irving, Tex.

[73] Assignee: Dexide, Inc., Fort Worth, Tex.

[*] Notice: The term of this patent shall not extend beyond the expiration date of Pat. No. 5,217,451.

[21] Appl. No.: 223,840

[22] Filed: Apr. 6, 1994

Related U.S. Application Data

[63] Continuation of Ser. No. 29,372, Mar. 8, 1993, abandoned, which is a continuation of Ser. No. 705,110, May 24, 1991, Pat. No. 5,217,451.

[51] Int. Cl.$^6$ ................................................. A61B 17/00
[52] U.S. Cl. ............................. 606/1; 606/198; 604/105; 604/164; 604/174
[58] Field of Search ............................. 604/174, 108, 604/109, 105, 107, 164, 165; 606/198, 1, 185; 600/204

[56] References Cited

U.S. PATENT DOCUMENTS

| | | | |
|---|---|---|---|
| 1,155,169 | 9/1915 | Starkweather | 604/105 |
| 1,665,790 | 4/1928 | Novack | 604/107 |
| 1,972,428 | 9/1934 | Richard | 604/105 |
| 4,655,219 | 4/1987 | Petruzzi | 606/206 |
| 4,994,079 | 2/1991 | Genese et al. | 606/206 |
| 4,995,868 | 2/1991 | Brazier | 604/105 |
| 5,002,557 | 3/1991 | Hasson | 606/191 |
| 5,122,122 | 6/1992 | Allgood | 604/174 |
| 5,147,378 | 9/1992 | Markham | 606/206 |
| 5,197,971 | 3/1993 | Bonutti | 606/198 |

FOREIGN PATENT DOCUMENTS

| | | | |
|---|---|---|---|
| 116823 | 3/1930 | Austria | 606/207 |
| 0427949A1 | 5/1991 | European Pat. Off. | A61B 17/11 |

*Primary Examiner*—Michael H. Thaler
*Attorney, Agent, or Firm*—Robert A. Felsman; Mark D. Perdue

[57] ABSTRACT

A trocar assembly is disclosed for use in inserting a laparoscopic instrument into the abdominal cavity during surgery and includes a cylindrical member activated by intermeshing gears to expand a cylindrical member having a normally retracted outer diameter when the trocar assembly is within the abdominal cavity, to resist withdrawing movement of the assembly from the abdominal cavity.

7 Claims, 2 Drawing Sheets

GEAR ACTIVATED TROCAR ASSEMBLY

This is a continuation of application Ser. No. 08/029,372, filed Mar. 8, 1993, now abandoned, which is a continuation of application Ser. No. 07/705,110, filed May 24, 1991, now U.S. Pat. No. 5,217,451.

BACKGROUND OF THE INVENTION

1. Field of the Invention

The present invention is directed to a medical device, and, more particularly, to a trocar assembly which can be inserted a short distance into the abdominal cavity and expanded to prevent the device from sliding in and out of a surgical incision.

2. Brief Description of the Prior Art

Endoscopic surgical procedures gain access to the inside of an anatomical cavity by first using an implement, such as a trocar spike, cannula or a needle having a sharpened point to pierce or puncture the bodily tissues, muscles, membranes, or the like, which may form a portion of or surround, the cavity wall.

Similarly, in many endoscopic procedures, a small incision may be made in the skin of a patient along the abdomen, for example, and the sharp point of a larger penetrating implement, such as a trocar spike of suitable length and diameter, may be inserted into the incision, and pushed until the point punctures the cavity wall. Thereafter, a sleeve is slid over the exterior surface of the implement into the puncture wound to serve as a lining for preserving the shape of the passageway created by the implement and for insertion of an endoscope, laparoscope, or the like, to view and operate upon organs within the cavity.

In many such applications, a trocar is used which incorporates a sleeve which may have a tendency to slide in and out of the incision in the abdominal wall, particularly when the surgeon is trying to move the laparoscopic instrument through the interior of the trocar sleeve into or out of the abdominal cavity.

One solution to such prior art deficiencies is discussed in U.S. patent application Ser. No. 440,199, filed Nov. 22, 1989, now U.S. Pat. No. 5,122,122, entitled "Locking Trocar Sleeve" and assigned to the same assignee as the present invention. In such application, concentric sleeves are disclosed, with the outer of the sleeves being manipulatable between contracted and expanded outer diameters to form a mushroom-like configuration at the distal end of the device which has been inserted into the abdominal cavity, such that resistance to withdrawal movements is effected when the surface of the mushroom contacts an abdominal wall. The activation of the mushroom is effected by a comparatively complex rotational or other mechanism, as disclosed. Moreover, the outer member which is "mushroomed" is not the member which, itself, is directly activated.

The present invention addresses the deficiencies of the prior art, as set forth above.

SUMMARY OF THE INVENTION

In the present invention, a trocar assembly is provided for use in inserting an endoscopic instrument into the abdominal cavity. The assembly comprises a housing with first and second elongate cylindrical members having first ends mounted through the housing. The cylindrical members are concentrically disposed relative to one another. One of the cylindrical members defines a passageway for receipt of an auxiliary surgical instrument therethrough. One of the cylindrical members has a second end with a first normally retracted external diameter selectively expandable to a second enlarged external diameter to resist withdrawal of the assembly from within an abdominal cavity when the external diameter of said one of the cylindrical members is selectively expanded. The one of the said members has a first gear member including first inter-engageable means, while a second gear member is carried on the housing and has a second inter-engageable means, such as intermeshing teeth, for companion interfacing with the first inter-engageable means.

The gear means are manually non-rotatably manipulatable to move the second end of the cylindrical member between the retracted and enlarged diameters.

DESCRIPTION OF THE PREFERRED EMBODIMENTS

Figure 1:
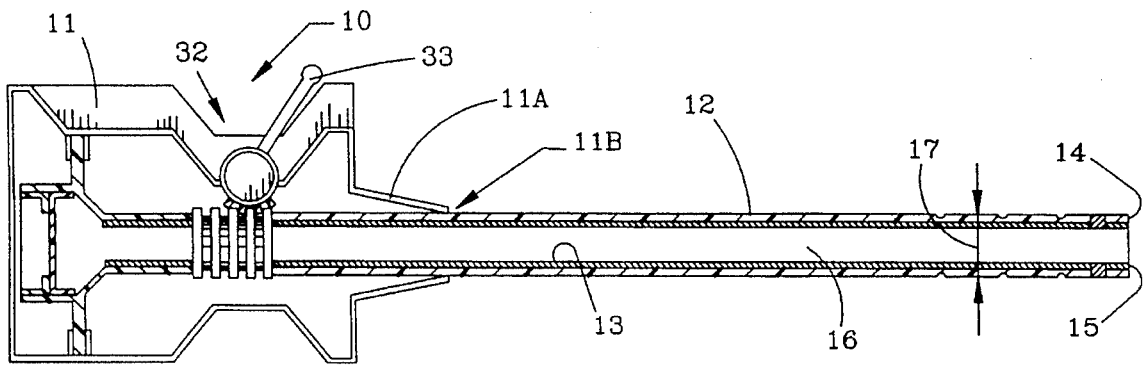
FIG. 1 is a sectional schematic illustration of the apparatus of the present invention in position prior to insertion into an abdominal cavity, with the cylindrical members being in normally retracted position relative to one another.

Now with first reference to FIG. 1, there is shown a trocar assembly 10 having a housing 11 with an upper opening 32 defined therein for receipt of the outwardmost end of a hand-manipulatable control assembly 33. The housing 10 has a distal end with an abutment skirt 11A thereon terminating in a receptacle 11B for receipt of first and second concentrically disposed cylindrical members 12 and 13 therethrough and into the housing 11.

A passageway 16 extends completely through the assembly 10 and the innermost of the cylindrical members 13 to an opening 15. An end 14 is defined on the distal end of the first elongate cylindrical member 12, which is inserted into the abdominal cavity. As shown in FIG. 1, the first elongate cylindrical member 12 has a retracted outer diameter 17.

Figure 2:
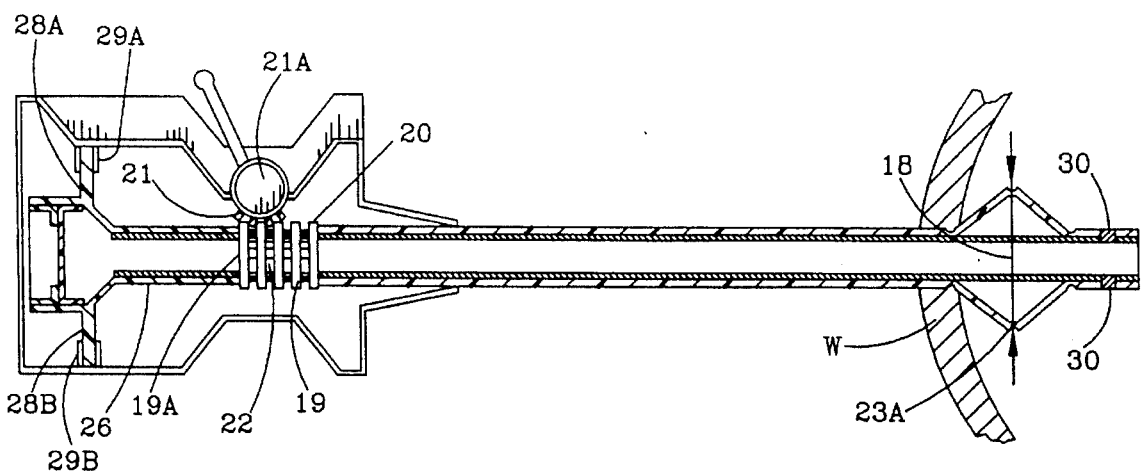
FIG. 2 is a view similar to that of FIG. 1, but illustrating the position of one of the cylindrical members relative to the other when the one cylindrical member's outer diameter is expanded, such as subsequent to insertion through the abdominal wall into the cavity, during surgery.

Now referring to FIG. 2, the first and second elongate cylindrical members 12 and 13 are secured, one to another by means of securements 30 radially spaced there-across at the distal end, such as by spot welding, or the like.

The first elongate cylindrical member 12 carries thereon a portion within the housing 11 defining a gear member 19 having inter-engaging teeth at 20 thereon and, preferably, in a spiral in an annular tooth configuration, 22. A cylindrical extension 26 has a no-go shoulder 27 (FIG. 3) thereon which contacts the end 19A of the gear member 19 when the cylindrical members 12, 13 are moved to the normally retracted position, as shown in FIG. 1, to thereby limit travel of the moving cylindrical member in one direction, i.e., when the cylindrical member 12 is moved by the lever 33 from the expanded position, FIG. 2, to the retracted position, FIG. 1.

Companion inter-engaging teeth members 21 are provided circularly around a portion of a ring component 21A of the lever 33 for inter-engagement with the teeth 20 on the gear member 19 of the first elongate cylindrical member 12.

Figure 4:
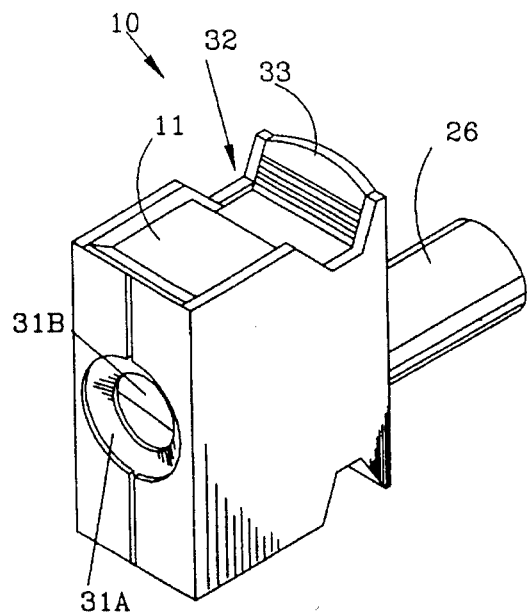
FIG. 4 is an outer perspective view of the apparatus of the present invention illustrating, in particular, the manual manipulating means through the housing and the seal assembly for insertion of an auxiliary instrument, such as a laparoscope.
Figure 5:
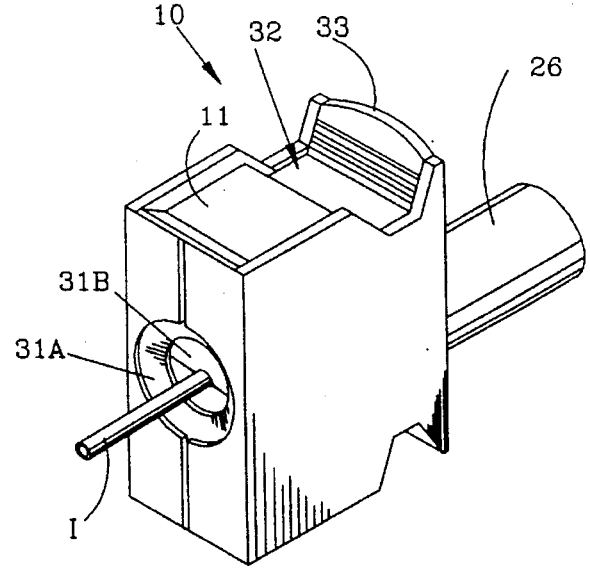
FIG. 5 is a view similar to that of FIG. 4, showing the insertion of an auxiliary instrument, such as the laparoscope.

The extension member 26 has a series of outwardly protruding wing members, 28A, 28B which are inserted in companion slots 29A, 29B on the housing 11 for securement thereto. An outer seal member 31A and companion lip seal 31B, as shown in FIG. 4, prevent transmission of gasses, and other fluids, from within the passageway 16, when the assembly 10 is within the abdominal cavity, during surgery.

An auxiliary instrument 1, such as a laparoscope, may be inserted through the seal member 31B and into the passageway 16, subsequent to insertion of the assembly 10 within the abdominal cavity and manipulation of the first elongate cylindrical member 12 to the expanded outer diameter 18, as shown in FIG. 2.

Figure 3:
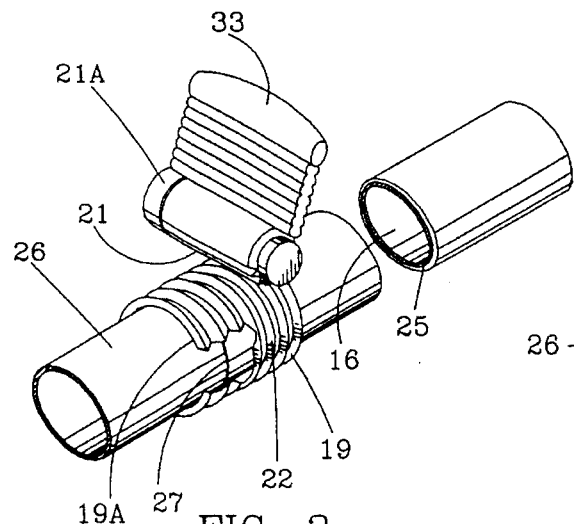
FIG. 3 is a prospective illustration of one of the cylindrical members and sleeve and an inter-engaging gear means.
Figure 3A:
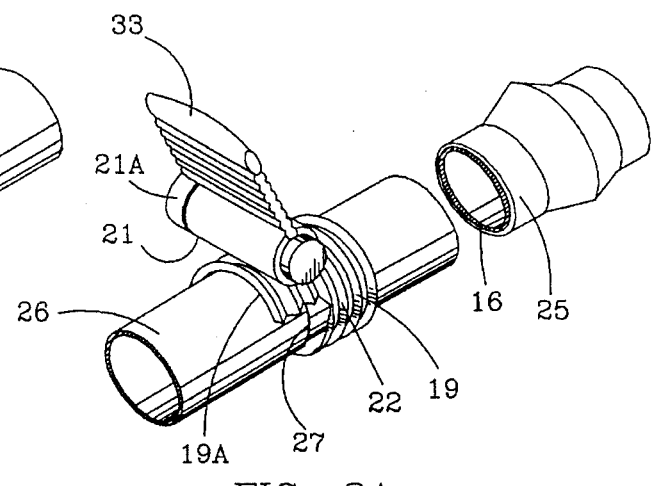
FIG. 3A is a view similar to that of FIG. 3, illustrating the position of the respective components during activation such that the outer cylindrical sleeve is in expanded position.

Now referring to FIGS. 3 and 3A, a sleeve portion 25 is defined immediate the distal end of the first elongate cylindrical member 12 and has a series of radially extending serrated flexing members 23 thereon with openings 24 inter-defined there between. A serration 23A is cut on each of the flexing members 23 to permit flexing movement to the expanding outer diameter position 18.

OPERATION

When it is desired to insert the trocar assembly 10 into the abdominal wall through an incision, or the like, during surgery, the assembly 10 is inserted therein by the surgeon simply grasping the housing 11 and inserting the assembly 10 through such incision, or opening. Thereafter, prior to introduction of the auxiliary instrument I through the assembly 10, the lateral and non-rotating lever 33 is contacted by the finger or thumb of the surgeon and moved from the position shown in FIG. 3, backwardly, to the position shown in FIG. 3A. Accordingly, as the control 33 is manipulated, the teeth 21 in the ring 21A will travel across the companion inter-engaging teeth 20 in the teeth configuration 22 of the gear member 19, such that the first elongate cylindrical member 12 moves non-rotatably and laterally away from the no-go shoulder 27 on the cylindrical extension 26. Because the first and second cylindrical members 12, 13 are attached one to another by means of the securements 30 at the distal end of the assembly 10, movement of the first elongate cylindrical member 12 relative to the second member, 13, will cause the sleeve portion 25 flexing members 23 to be urged radially outwardly from the cylindrical member 12 from the retracted outer diameter of position 17 (FIG. 1) to the expanded outer diameter of 18 (FIG. 2). In the position shown in FIG. 2, the trocar assembly 10 thus resists removal from the abdominal wall W in the cavity, during surgery.

The apparatus may be moved from the position shown in FIG. 2 to the position shown in FIG. 1 by reversing the procedure described above, and the assembly 10 completely withdrawn from the abdominal wall W.

Although the invention has been described in terms of specified embodiments which are set forth in detail, it should be understood that this is by illustration only and that the invention is not necessarily limited thereto, since alternative embodiments and operating techniques will become apparent to those skilled in the art and view of the disclosure. Accordingly, modifications are contemplated which can be made without departing from the spirit of the described invention.

What is claimed and desired to be secure by Letters Patent is:

1. A sleeve for insertion of a surgical instrument into a bodily cavity through an incision in a body, the sleeve comprising:

a housing;

an outer cylindrical member coupled to the housing and including a radially expandable member thereon for selective expansion to resist removal of the sleeve from the bodily cavity;

an inner cylindrical member concentrically disposed within the outer cylindrical member and secured thereto, the inner cylindrical member being secured to and stationary relative to the housing and having a passage extending therethrough for passage of the surgical instrument;

a lever carried by the housing and coupled to the outer cylindrical member by gear teeth on the outer cylindrical member and inter-engaging gear teeth on the lever, wherein manipulation of the lever causes the outer sleeve to move relative to the housing and inner sleeve and the selective expansion of the radially expandable member; and a seal means carried in the passage to prevent escape of fluids from the bodily cavity.

2. The surgical sleeve according to claim 1 wherein the radially expandable member comprises a series of serrated flexing members formed on the outer cylindrical member.

3. The surgical sleeve according to claim 1 wherein the seal means is a lip seal.

4. A sleeve for insertion of a surgical instrument into a bodily cavity through an incision in a body, the sleeve comprising:

a housing;

an outer cylindrical member coupled to the housing and including a series of radially expandable flexing members for selective expansion to resist removal of the sleeve from the bodily cavity, the outer cylindrical member having gear teeth at its upper end;

an inner cylindrical member concentrically disposed within the outer cylindrical member and secured thereto, the inner cylindrical member being secured to and stationary relative to the housing and having a passage extending therethrough for passage of the surgical instrument;

a lever pivotally coupled to the housing and coupled to the outer cylindrical member by gear teeth on the lever inter-engaging with those on the outer cylindrical member to cause the outer cylindrical member to move relative to the housing and inner cylindrical member and the selective expansion of the radially expandable member; and a seal means carried in the passage to prevent escape of fluids from the bodily cavity.

5. The surgical sleeve according to claim 4 wherein the seal means is a lip seal.

6. A sleeve for insertion of a surgical instrument into a bodily cavity through an incision in a body, the sleeve comprising:

a housing;

an outer cylindrical member coupled to the housing and including a series of radially expandable flexing members for selective expansion to resist removal of the sleeve from the bodily cavity;

a gear member carried by the outer cylindrical member;

an inner cylindrical member concentrically disposed within the outer cylindrical member and secured thereto, the inner cylindrical member being secured to and stationary relative to the housing and having a passage extending therethrough for passage of the surgical instrument;

a lever pivotally mounted to the housing and having gear teeth thereon for interengagement with the gear member on the outer cylindrical member to cause the outer cylindrical member to move relative to the housing and inner sleeve and the selective expansion of the radially expandable flexing members; and a lip seal carried in the passage to prevent escape of fluids from the bodily cavity.

7. The surgical sleeve according to claim 6 wherein the gear member on the outer cylindrical member comprises a helically threaded ring.

* * * * *